United States Patent
Lee et al.

(10) Patent No.: US 10,568,562 B2
(45) Date of Patent: Feb. 25, 2020

(54) ELECTRONIC APPARATUS AND METHOD FOR PROVIDING SKIN INSPECTION INFORMATION THEREOF

(71) Applicant: CAL-COMP BIG DATA, INC., New Taipei (TW)

(72) Inventors: Dai-Jung Lee, New Taipei (TW); Chia-Ming Yong, New Taipei (TW); Hung-Tai Hsu, New Taipei (TW); Ching-Sheng Tsai, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 73 days.

(21) Appl. No.: 15/371,210

(22) Filed: Dec. 7, 2016

(65) Prior Publication Data

US 2018/0085048 A1    Mar. 29, 2018

(30) Foreign Application Priority Data

Sep. 29, 2016   (TW) .............................. 105131281 A

(51) Int. Cl.
*A61B 5/00* (2006.01)
*G06K 9/00* (2006.01)
(Continued)

(52) U.S. Cl.
CPC .............. *A61B 5/442* (2013.01); *A45D 44/00* (2013.01); *A61B 5/0077* (2013.01); *A61B 5/444* (2013.01);
(Continued)

(58) Field of Classification Search
CPC ....... A61B 5/442; A61B 5/444; A61B 5/0077; G06K 9/00268; G06K 9/00255;
(Continued)

(56) References Cited

U.S. PATENT DOCUMENTS 9,427,187 B2 *  8/2016  Gilbert ................. A61B 5/0059
9,449,400 B2 *  9/2016  Stephan ............... A61B 5/0077
(Continued)

FOREIGN PATENT DOCUMENTS

CN        101686819        8/2014
TW        201116257        5/2011

OTHER PUBLICATIONS

"Office Action of Taiwan Counterpart Application," dated May 8, 2017, p. 1-p. 9, in which the listed references were cited.

*Primary Examiner* — Bobbak Safaipour
(74) *Attorney, Agent, or Firm* — JCIPRNET

(57) ABSTRACT

An electronic apparatus and a method for providing skin inspection information thereof are provided. The method includes the following steps. If it is determined that current measurement information is received, a result assessment page showing a detection result of the current measurement information is displayed via a screen, to show whether the detection result achieves a skin goal via the result assessment page. A skin overview page is displayed in response to receipt of an operation performed on the result assessment page. A goal setting page is displayed via the screen in response to receipt of a first operation performed on the skin overview page, and setting of the skin goal is received via the goal setting page. A detail analysis page associated with one of skin parameters is displayed via the screen in response to receipt of a second operation performed on the skin overview page.

15 Claims, 17 Drawing Sheets

(51) Int. Cl.
*G06F 3/0482* (2013.01)
*G06F 3/0484* (2013.01)
*G06F 3/0483* (2013.01)
*A45D 44/00* (2006.01)

(52) U.S. Cl.
CPC .......... *G06F 3/0482* (2013.01); *G06F 3/0483* (2013.01); *G06F 3/0484* (2013.01); *G06K 9/00255* (2013.01); *G06K 9/00268* (2013.01); *A45D 2044/007* (2013.01)

(58) Field of Classification Search
CPC ............. A45D 44/00; A45D 2044/007; G06F 3/0482; G06F 3/0483; G06F 3/0484
See application file for complete search history.

(56) References Cited

U.S. PATENT DOCUMENTS

| | | | |
|---|---|---|---|
| 2009/0201365 A1 | 8/2009 | Fukuoka et al. | |
| 2009/0245603 A1* | 10/2009 | Koruga | A45D 44/00 382/128 |
| 2014/0275948 A1* | 9/2014 | Kamisoyama | A61B 5/6898 600/407 |
| 2015/0213619 A1* | 7/2015 | Nakamura | A61B 5/0077 382/128 |
| 2016/0055758 A1* | 2/2016 | Francis | G09B 5/02 434/236 |
| 2017/0035348 A1* | 2/2017 | Bandic | G16H 15/00 |
| 2017/0119301 A1* | 5/2017 | Kimura | G06T 7/0012 |
| 2018/0088778 A1* | 3/2018 | Yong | G16H 40/60 |
| 2018/0125201 A1* | 5/2018 | Nichols | A46B 5/0095 |
| 2019/0053607 A1* | 2/2019 | Shen | G06K 9/00255 |
| 2019/0059561 A1* | 2/2019 | Shen | A45D 44/00 |
| 2019/0059806 A1* | 2/2019 | Shen | G06K 9/00248 |
| 2019/0065827 A1* | 2/2019 | Shen | G06T 11/60 |

* cited by examiner

ELECTRONIC APPARATUS AND METHOD FOR PROVIDING SKIN INSPECTION INFORMATION THEREOF

CROSS-REFERENCE TO RELATED APPLICATION

This application claims the priority benefit of Taiwan application serial no. 105131281, filed on Sep. 29, 2016. The entirety of the above-mentioned patent application is hereby incorporated by reference herein and made a part of this specification.

BACKGROUND

Technical Field

The disclosure relates to technology of inspecting a skin state and particularly relates to an electronic apparatus and a method of providing skin inspection information thereof.

Description of Related Art

The traditional skin inspection relies on use of a professional skin inspection instrument for scanning the skin, so as to obtain information about the skin condition. Sales staff may recommend suitable skin care products according to the skin condition so as to promote their products. However, it may not be easy for the user to buy a skin inspector of his/her own. The reason is that skin inspectors are expensive and large in size. Moreover, the skin inspector is equipped with microscope heads of different magnifications for scanning and capturing images of the skin. Since only a small area of the skin is scanned each time, operation of the skin inspector would take a long time. In addition, it requires professional training to use the skin inspector to assess the skin condition. For these reasons, the skin inspector may not meet the needs of those who want to know whether their skin or skin conditions have improved from time to time.

Some users may want to know if the skin care products they are using are indeed improving the skin conditions, but they can only assess the skin conditions with naked eyes through the mirror. Such assessment may not be reliable for it may be affected by psychological factors and environmental factors, and it may cause the users to waste more money on skin care products they don't need. Hence, how to check and inspect the skin condition and keep a record of the skin care process is one of the functions that the users who desire skin improvement want.

SUMMARY

In view of the above, the disclosure provides an electronic apparatus and a method of providing skin inspection information thereof, by which the user is able to obtain accurate and reliable skin inspection information to be used as reference for facial skin care by performing simple operations.

In an embodiment of the disclosure, a method of providing skin inspection information is provided, which is adapted for an electronic apparatus that includes an image capturing device and a screen. The method includes the following: if it is determined that current measurement information of a facial skin is received, a result assessment page of a detection result of the current measurement information is displayed via the screen, so as to show whether the detection result achieves a skin goal via the result assessment page; in response to receipt of an operation performed on the result assessment page, a skin overview page is displayed via the screen, wherein the skin overview page displays a plurality of skin parameters of the facial skin; in response to receipt of a first operation performed on the skin overview page, a goal setting page is displayed via the screen, and setting of the skin goal is received via the goal setting page; and in response to receipt of a second operation performed on the skin overview page, a detail analysis page associated with one of the skin parameters is displayed via the screen.

From another aspect, the disclosure provides an electronic apparatus, which includes an image capturing device, a screen, a storage device, and a processor. The processor is coupled to the image capturing device, the screen, and the storage device. If the processor determines that current measurement information of a facial skin is received, the processor displays a result assessment page of a detection result of the current measurement information via the screen, so as to show whether the detection result achieves a skin goal via the result assessment page. In response to receipt of an operation performed on the result assessment page, the processor displays a skin overview page via the screen, wherein the skin overview page displays a plurality of skin parameters of the facial skin. In response to receipt of a first operation performed on the skin overview page, the processor displays a goal setting page via the screen and receives setting of the skin goal via the goal setting page, and in response to a second operation performed on the skin overview page, the processor displays a detail analysis page associated with one of the skin parameters via the screen.

Based on the above, in an embodiment of the disclosure, when the user wants to obtain the skin inspection information, the electronic apparatus shows whether the current detection result achieves the skin goal via the result assessment page first. Then, in response to receipt of the operation performed on the result assessment page, the electronic apparatus displays the skin overview page including the radar diagram of multiple skin parameters via the screen. Further, in response to receipt of the first operation or the second operation performed on the skin overview page, the electronic apparatus displays the goal setting page or the detail analysis page of any one of the skin parameters via the screen. Therefore, through arrangement and design of each displayed page, the user is able to obtain accurate and objective skin inspection information by performing simple operations.

To make the aforementioned and other features and advantages of the disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
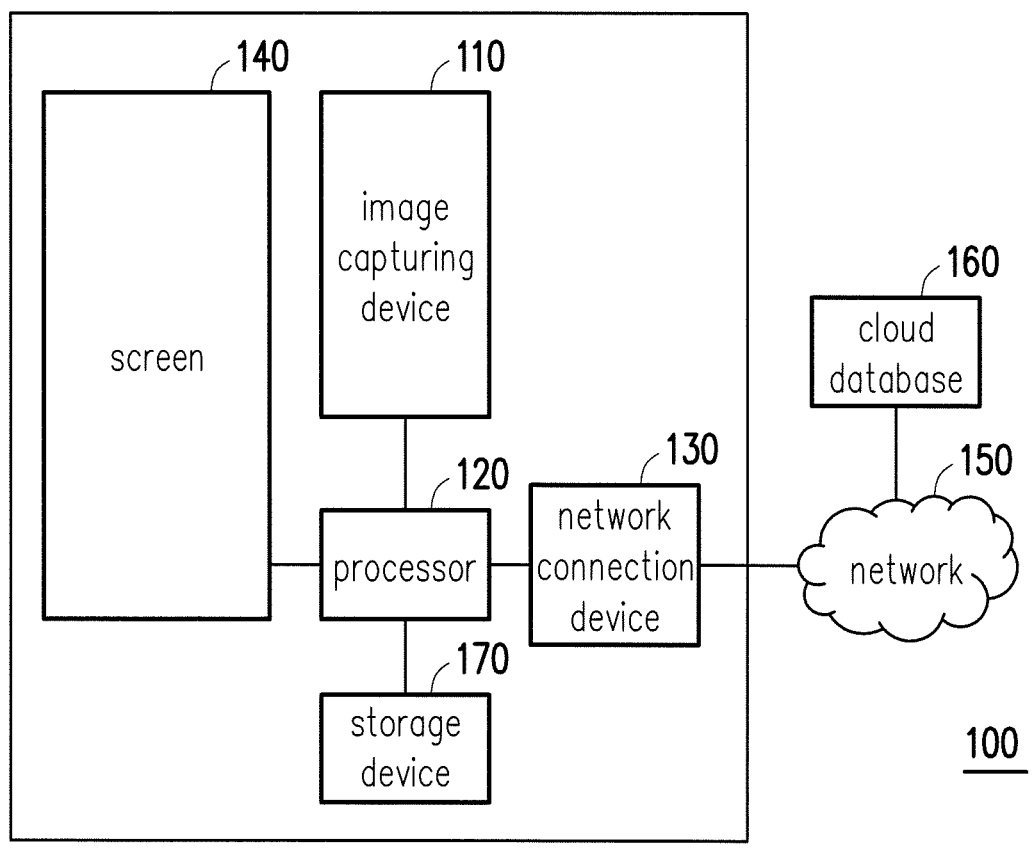
FIG. 1 is a schematic diagram showing the electronic apparatus according to an embodiment of the disclosure.

FIG. 1 is a schematic diagram showing an electronic apparatus according to an embodiment of the disclosure. FIG. 1 is a schematic diagram of an electronic apparatus 100 according to an embodiment of the disclosure. The electronic apparatus 100 includes an image capturing device 110, a processor 120, a network connection device 130, a screen 140, and a storage device 170. The processor 120 is coupled to the image capturing device 110, the network connection device 130, the screen 140, and the storage device 170. The electronic apparatus 100 according to the embodiment of the disclosure may be a device disposed on a dressing table. The screen 140 of the electronic apparatus 100 may be disposed behind a mirror, and text or an image displayed by the screen 140 may be seen by the user through the mirror. In other embodiments, the electronic apparatus 100 may be a consumer electronics product, such as a smart phone, a tablet computer, and so on, or a portable mirror box combined with a portable mirror.

The processor 120 may be a central processing unit (CPU), a programmable microprocessor for general use or special use, a digital signal processor (DSP), a programmable controller, an application specific integrated circuit (ASIC), other similar devices, or a combination of the foregoing.

The image capturing device 110 may be a camera or a video recorder for capturing images to obtain facial information of the current user. The processor 120 is connected to a network 150 via the network connection device 130. The network connection device 130 may be a network chip or a network card that supports one or more network communication protocols, such as wireless network protocol, Bluetooth protocol, and so on. In this embodiment, the network 150 is connected to a cloud database 160. The cloud database 160 may include personal information (such as age, location, and so on) of multiple users and skin inspection information for facial skin care.

The screen 140 may be a display device that provides a display function in a display area of the electronic apparatus 100. The screen 140 may be a display screen device that provides a display function, such as a liquid crystal display (LCD), a light-emitting diode (LED) display, a field emission display (FED), and so on.

The storage device 170 is a stationary or movable random access memory (RAM) in any form, a read-only memory (ROM), a flash memory, other similar devices, or a combination of these devices, for example. The storage device 170 is used to record a plurality of commands to be executed by the processor 120, and the commands may be loaded into the processor 120. The storage device 170 may also store the skin inspection information of the user.

Moreover, according to the disclosure, data may be inputted via a touch screen 140 or an external input device (not shown), such as a mouse, a keyboard, a joystick, a touch panel, and so on. Data may also be inputted by gesture recognition performed by the image capturing device 110, or by voice control. Nevertheless, the disclosure is not limited to the foregoing.

Steps of a method of providing the skin inspection information in accordance with the embodiment of the disclosure may be implemented by chip hardware or firmware in the electronic apparatus, or by software or application programs stored in the storage device 170 to be executed by the processor 120 of the electronic apparatus 100.

Figure 2:
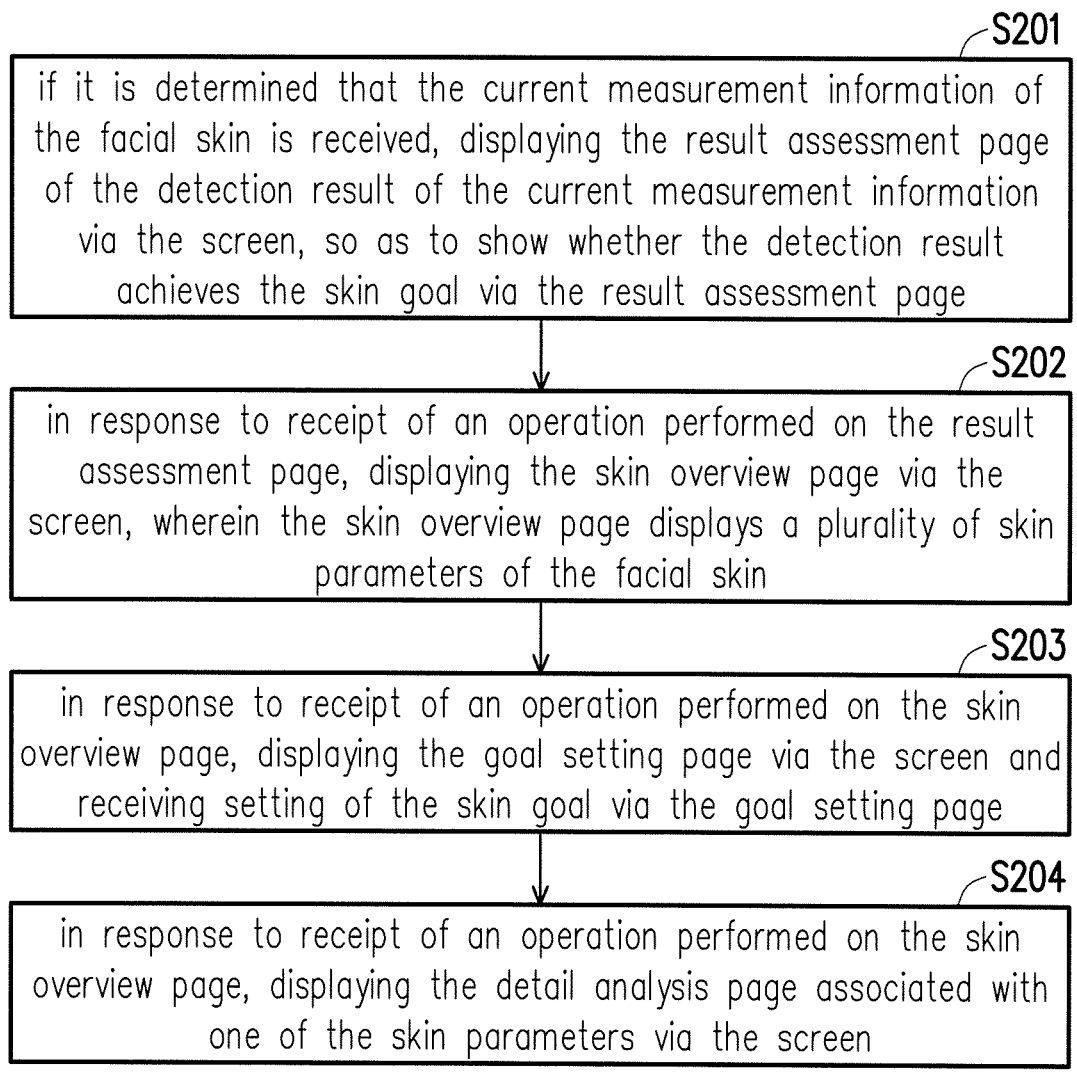
FIG. 2 is a flowchart showing the method of providing skin inspection information according to an embodiment of the disclosure.

FIG. 2 is a flowchart showing the method of providing the skin inspection information according to an embodiment of the disclosure. Referring to FIG. 1 and FIG. 2, the method of this embodiment is adapted for the electronic apparatus 100 described in the above embodiment. Steps of the method of providing the skin inspection information according to this embodiment are described in detail hereinafter with reference to the components of the electronic apparatus 100.

It should be noted that, in the embodiment of the disclosure, the electronic apparatus 100 captures an image of the facial skin of the user via the image capturing device 110 and obtains current measurement information of the facial skin by analyzing the facial image of the user. In Step S201, if the processor 120 determines that the current measurement information of the facial skin is received, the processor 120 displays a result assessment page of a detection result of the current measurement information via the screen 140, so as to show whether the detection result achieves a skin goal via the result assessment page. It should be noted that, the depiction of the processor displaying any one of pages is referring as the processor controlling the screen to display any one of pages. Here, the current measurement information is defined as measurement information of the facial skin that is obtained in a predetermined time interval. The predetermined time interval may be a few hours, one day, two days, three days, and so on, depending on a sampling frequency desired by the user. Nevertheless, the disclosure is not intended to limit the predetermined time interval. Here, the predetermined time interval is one day, for example. By determining whether the measurement information of the facial skin is received on the day when the user operates the electronic apparatus 100, the processor 120 decides whether the current measurement information of the facial skin is received.

Specifically, when the user starts using the electronic apparatus 100, the processor 120 directly displays the result assessment page of the detection result of the current measurement information after determining that the current measurement information of the facial skin is received. On the other hand, if the processor 120 determines that the current measurement information of the facial skin is not received, the processor 120 prompts the user to capture an image of the facial skin, so as to obtain the current measurement information of the facial skin. Moreover, the processor 120 compares a skin goal that is predetermined or set by the user with the current measurement information to obtain the detection result of the current measurement information. Then, the processor 120 shows whether the detection result achieves the skin goal via the result assessment page. The skin goal includes one of a plurality of skin parameters and a corresponding achievement value. Thereby, the user is able to learn the progress of improvement of the skin condition quickly.

Here, the current measurement information includes a plurality of skin parameters related to the skin, which are calculated based on severity of a plurality of variable features of the skin obtained by analyzing different areas of the facial image of the user. The variable features include wrinkles, facial lines, erythema, acne, spots, pores, skin color, dark circle, and so on, for example. The processor 120 of the electronic apparatus 100 obtains the variable features by a particular determination criterion and severity, and calculates the skin parameters based on the variable features. The skin parameters are common determination standards in the field of skin care. The skin parameters include skin clarity, texture, firmness, brightness, healthiness, and so on, for example.

Next, in Step S202, in response to receipt of an operation performed on the result assessment page, the processor 120 displays a skin overview page via the screen 140, wherein the skin overview page displays a plurality of skin parameters of the facial skin. Thereby, after confirming the progress of improvement of the skin condition via the result assessment page, the user is able to intuitively and clearly learn the current overall condition of the facial skin via the skin overview page.

Thereafter, in Step S203, in response to receipt of a first operation performed on the skin overview page, the processor 120 displays a goal setting page via the screen 140 and receives setting of a skin goal via the goal setting page. In addition, in Step S204, in response to receipt of a second operation performed on the skin overview page, the processor 120 displays a detail analysis page associated with one of the skin parameters via the screen 140. That is, after the user clearly understands the current overall condition of the facial skin via the skin overview page, the user may select to set the skin goal via the goal setting page or further check out a detail analysis of one of the skin parameters via the detail analysis page. By Steps S201 to S204, the user is able to obtain the skin inspection information of the facial skin quickly with use of the electronic apparatus 100 and know whether the facial skin achieves the skin goal.

FIG. 3A to FIG. 3D are flowcharts showing details of a method of providing skin inspection information according to an embodiment of the disclosure. The method of this embodiment is adapted for the electronic apparatus 100 described in the above embodiment. Steps of the method of providing the skin inspection information according to this embodiment are described in detail hereinafter with reference to the components of the electronic apparatus 100.

Figure 3A:
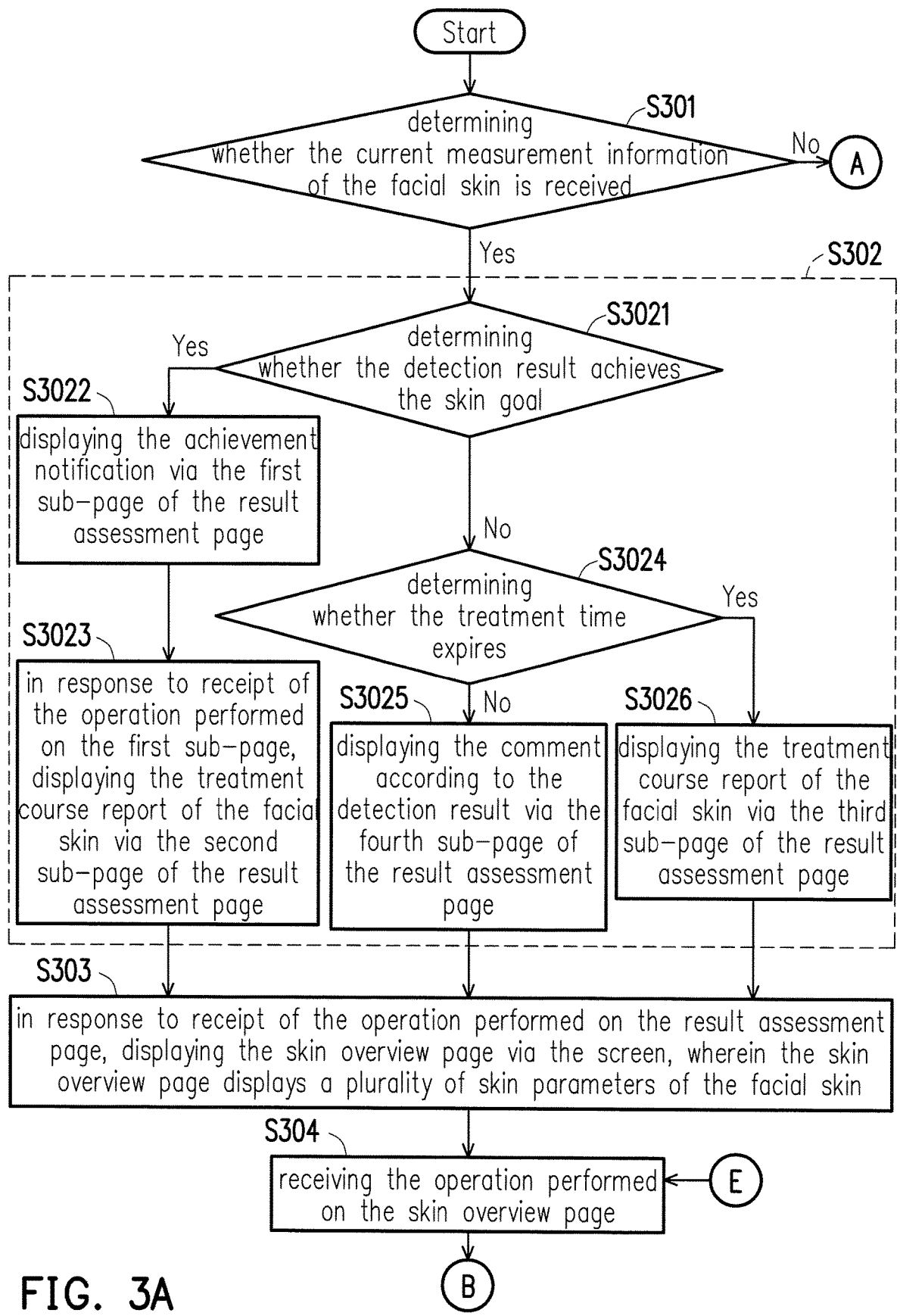
FIG. 3A to FIG. 3D are flowcharts showing details of the method of providing skin inspection information according to an embodiment of the disclosure.
Figure 4:
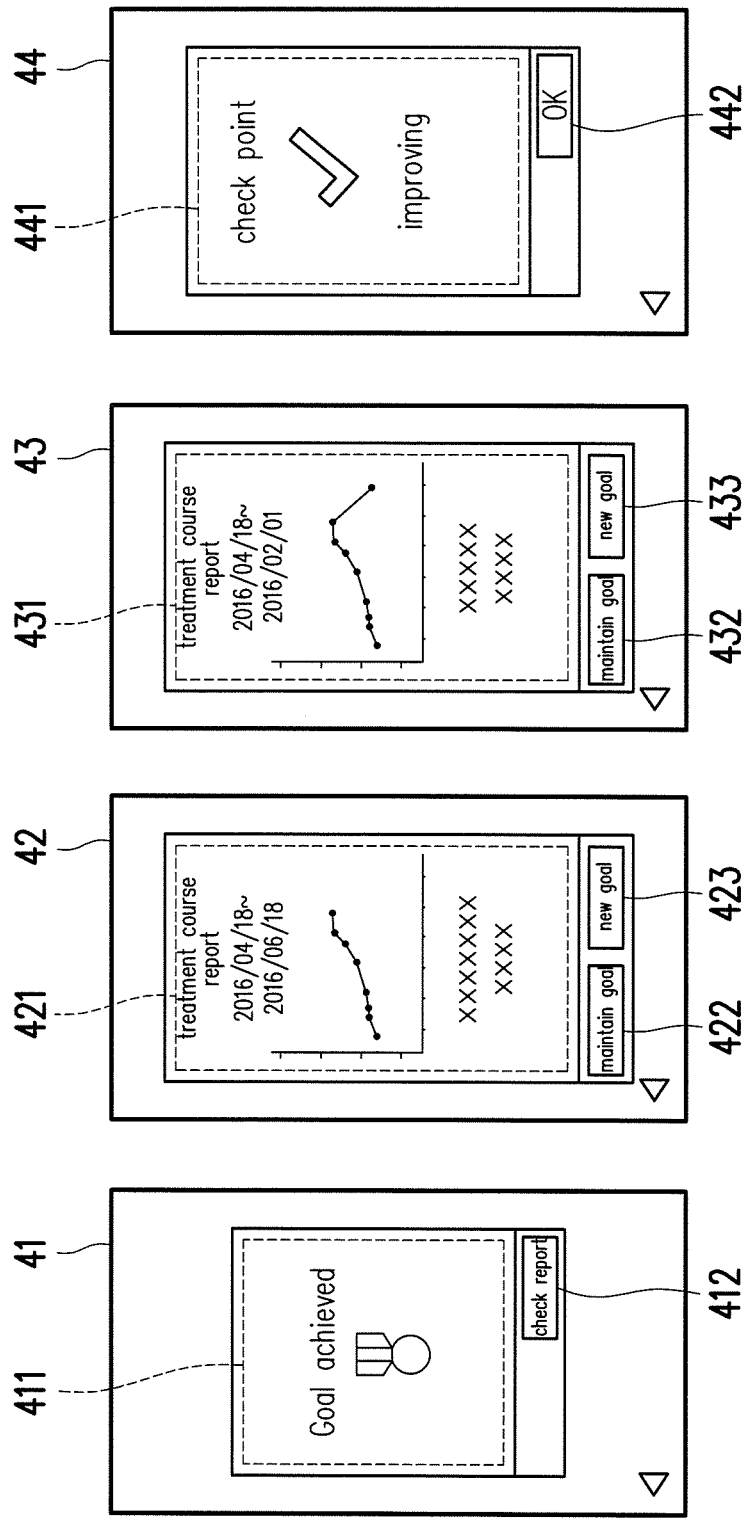
FIG. 4 is a schematic diagram showing the result assessment page according to an embodiment of the disclosure.

Referring to FIG. 3A, in Step S301, the processor 120 determines whether the current measurement information of the facial skin is received. If the result of Step S301 is YES, in Step S302, the processor 120 displays the result assessment page of the detection result of the current measurement information via the screen 140, so as to show whether the detection result achieves the skin goal via the result assessment page. In this embodiment, Step S302 is further divided into Sub-steps S3021 to S3026 to be implemented. Referring to FIG. 3A and FIG. 4, FIG. 4 is a schematic diagram showing the result assessment page according to an embodiment of the disclosure.

First, in Step S3021, the processor 120 determines whether the detection result achieves the skin goal. If the result of Step S3021 is YES, in Step S3022, the processor 120 displays an achievement notification 411 via a first sub-page 41 of the result assessment page. The achievement notification 411 may include text or an image, but the disclosure is not limited thereto. Thereafter, in Step S3023, in response to receipt of an operation performed on the first sub-page 41, a treatment course report 421 of the facial skin is displayed via a second sub-page 42 of the result assessment page. For example, the user may perform a touch operation on an icon 412 to drive the processor 120 to control the screen 140 to display the second sub-page 42 of the result assessment page. The second sub-page 42 displays the treatment course report 421, an icon 422, and an icon 423. The treatment course report 421 provides the user a historical record related to one skin parameter through a chart, text, or a combination of the foregoing. The chart may be a line chart, a bar chart, and so on, for example, but the disclosure is not limited thereto. Moreover, the user may perform a touch operation on the icon 422 to drive the processor 120 to control the screen 140 to display the skin overview page. The user may also perform a touch operation on the icon 423 to drive the processor 120 to control the screen 140 to display the goal setting page, so as to receive an updated setting of the skin goal.

If the result of Step S3021 is NO, in Step S3024, the processor 120 determines whether a treatment time expires. To be more specific, the user sets the treatment time for performing a treatment in the electronic apparatus 100 by himself/herself. The "treatment time" may be set to one week, one month, three months, half a year, one year, or two years, for example. Generally, the user executes a particular treatment (e.g., using the same skin care product and skin care procedure) in the treatment time, so as to confirm whether the skin care product and the skin care procedure the user uses improve the skin condition in the treatment time. If the result of Step S3024 is YES, in Step S3026, the processor 120 displays a treatment course report 431 of the facial skin via a third sub-page 43 of the result assessment page. The third sub-page 43 displays the treatment course report 431, an icon 432, and an icon 433. The treatment course report 431 provides the user a historical record related to one skin parameter through a chart, text, or a combination of the foregoing. Moreover, the user may perform a touch operation on the icon 433 to drive the processor 120 to control the screen 140 to display the skin overview page. The user may also perform a touch operation on the icon 432 to drive the processor 120 to control the screen 140 to display the goal setting page, so as to receive an updated setting of the skin goal and start a new treatment.

If the result of Step S3024 is NO, in Step S3025, the processor 120 displays a comment 441 according to the detection result via a fourth sub-page 44 of the result assessment page. The fourth sub-page 44 displays the comment 441 and an icon 442. The user may perform a touch operation on the icon 442 to drive the processor 120 to control the screen 140 to display the skin overview page.

In an embodiment, the processor 120 determines whether a current time point matches a check time point. If the current time point matches the check time point, the processor 120 displays the fourth sub-page 44 of the result assessment page via the screen 140. If the current time point does not match the check time point, the processor 120 directly displays the skin overview page via the screen 140. In other words, the fourth sub-page 44 of the result assessment page is displayed or not according to whether the current time point matches the check time point. Here, the check time point is a particular time point in a treatment period. For example, the check time point refers to a plurality of particular dates that are decided every two days after the treatment starts.

Figure 5:
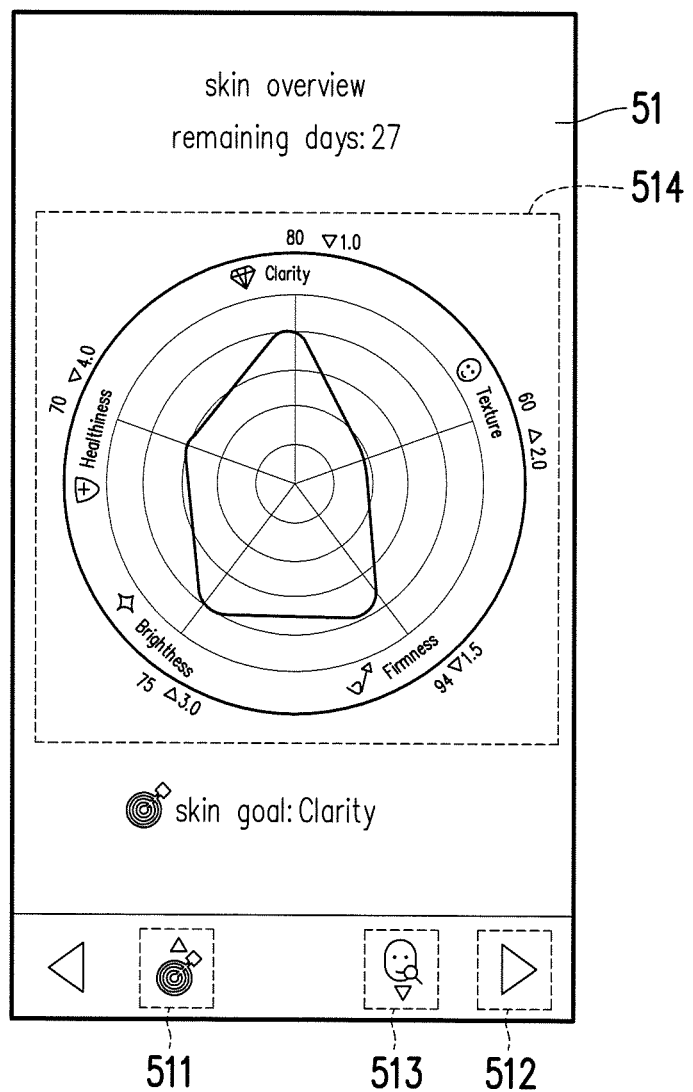
FIG. 5 is a schematic diagram showing the skin overview page according to an embodiment of the disclosure.

Thereafter, in Step S303, in response to receipt of an operation performed on the result assessment page, the processor 120 displays the skin overview page via the screen 140, wherein the skin overview page displays a plurality of skin parameters of the facial skin. Take FIG. 4 as an example, the operation performed on the result assessment page may be a touch operation that the user performs on the icon 422, the icon 433, or the icon 442. Referring to FIG. 5, FIG. 5 is a schematic diagram showing the skin overview page according to an embodiment of the disclosure. The skin overview page 51 displays a radar diagram 514 that is drawn according to the skin parameters, i.e., clarity, texture, thinness, brightness, and healthiness. The user learns the condition of the facial skin with respect to each skin parameter by reading the radar diagram 514. Moreover, the skin overview page 51 also displays that the skin goal currently selected by the user is "clarity." In addition, the skin overview page 51 also displays an icon 511, an icon 512, and an icon 513.

In Step S304, the processor 120 receives an operation performed on the skin overview page 51. The operation performed on the skin overview page 51 may be a touch operation that the user performs on the icon 511, the icon 512, or the icon 513 by a finger or a touch input device. Here, the user performs a touch operation on the icon 511 to drive the processor 120 to control the screen 140 to display the goal setting page. The user may perform a touch operation on the icon 512 to drive the processor 120 to control the screen 140 to display the detail analysis page of a particular skin parameter. The user may also perform a touch operation on the icon 513 to drive the processor 120 to control the screen 140 to display the measurement prompt page.

Figure 3B:
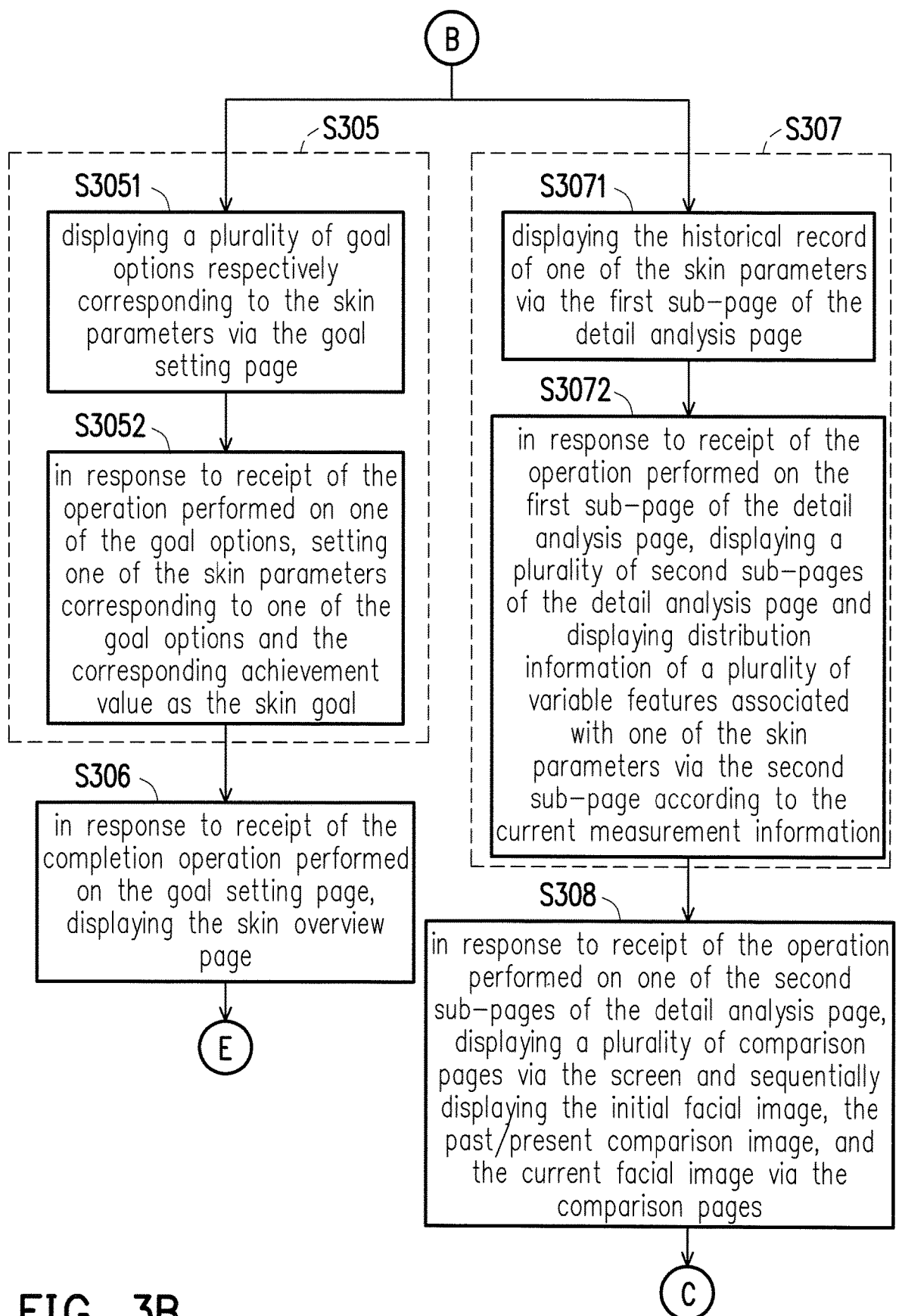
Figure 6:
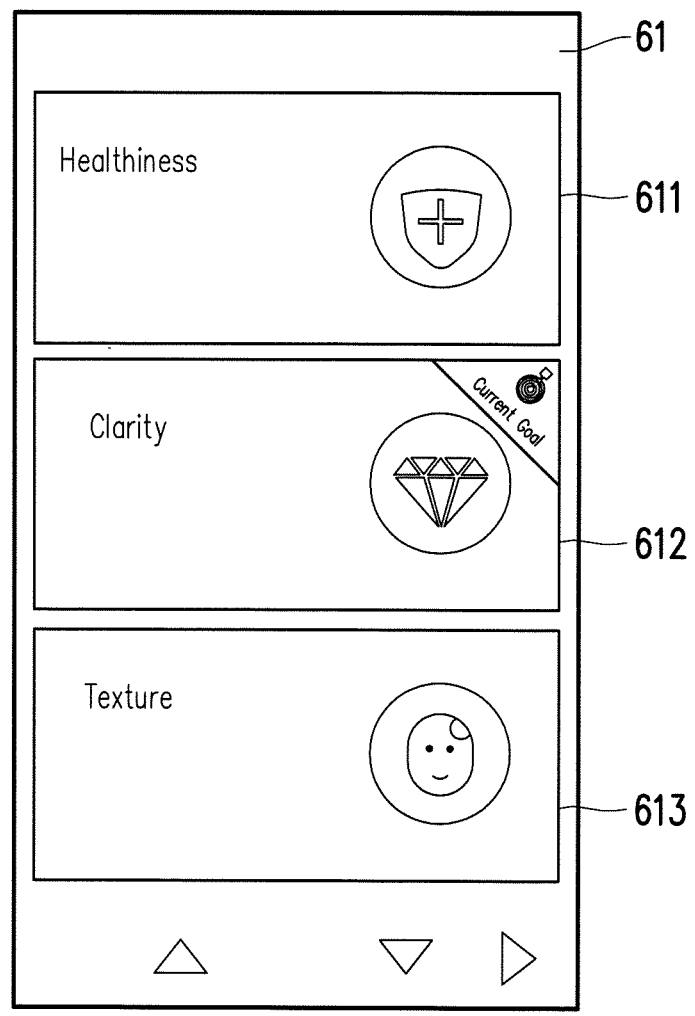
FIG. 6 is a schematic diagram showing the goal setting page according to an embodiment of the disclosure.

Referring to FIG. 3B, in response to the first operation performed on the skin overview page, in Step S305, the processor 120 displays the goal setting page via the screen 140 and receives setting of a skin goal via the goal setting page. Take FIG. 5 as an example, the first operation performed on the skin overview page is a touch operation that the user performs on the icon 511, for example. In this embodiment, Step S305 is divided into Sub-steps S3051 to S3052 to be implemented. Referring to FIG. 3B and FIG. 6, FIG. 6 is a schematic diagram showing the goal setting page according to an embodiment of the disclosure. In Step S3051, the processor 120 displays a plurality of goal options 611 to 613 respectively corresponding to the skin parameters via the goal setting page 61. In Step S3052, in response to receipt of an operation performed on one of the goal options 611 to 613, the processor 120 sets one of the skin parameters corresponding to the one of the goal options 611 to 613 and the corresponding achievement value as the skin goal. Take FIG. 6 as an example, when the user performs a touch operation on the goal option 612, the processor 120 sets the skin parameter "clarity" corresponding to the goal option 612 and the corresponding achievement value as the skin goal.

In Step S306, in response to receipt of a completion operation performed on the goal setting page 61, the processor 120 displays the skin overview page (e.g., the skin overview page 51). The completion operation performed on the goal setting page 61 is a touch operation that the user performs on an icon 614, for example. In addition, in an embodiment, after receiving the operation performed on one of the goal options 611 to 613, the processor 120 displays a goal setting confirmation page via the screen 140. At the moment, the processor 120 also displays the skin overview page in response to receipt of a completion operation performed on the goal setting confirmation page.

Figure 7:
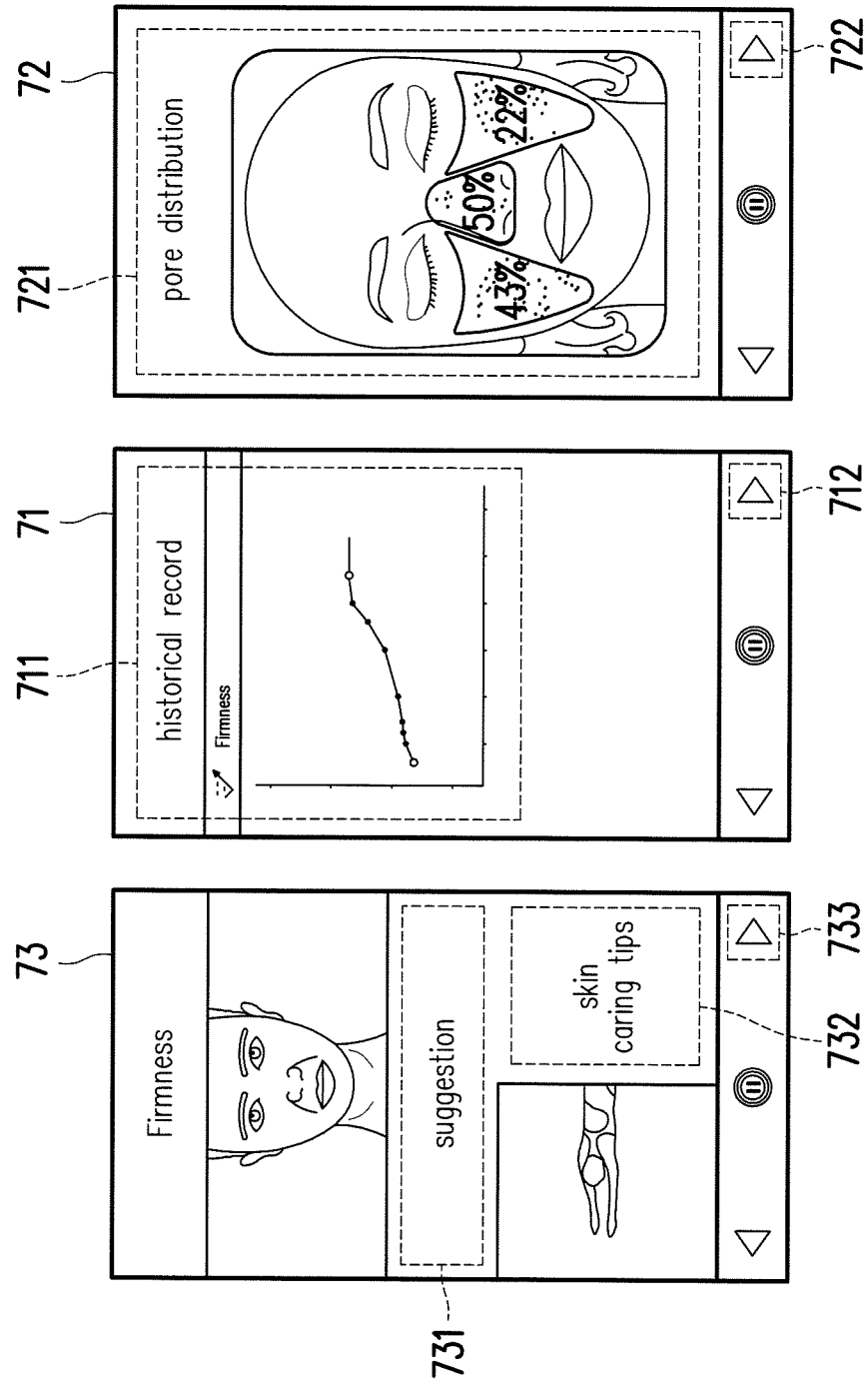
FIG. 7 is a schematic diagram showing the detail analysis page according to an embodiment of the disclosure.

Further, in response to receipt of the second operation performed on the skin overview page, in Step S307, the processor 120 displays the detail analysis page of one of the skin parameters via the screen 140. Take FIG. 5 as an example, the second operation performed on the skin overview page is a touch operation that the user performs on the icon 512, for example. In this embodiment, Step S307 is divided into Sub-steps S3071 to S3072 to be implemented. Referring to FIG. 3B and FIG. 7, FIG. 7 is a schematic diagram showing the detail analysis page according to an embodiment of the disclosure. In Step S3071, the processor 120 displays a historical record 711 of one of the skin parameters via a first sub-page 71 of the detail analysis page. In Step S3072, in response to receipt of an operation performed on the first sub-page 71 of the detail analysis page, which is a touch operation performed on an icon 712 of the first sub-page 71 for example, the processor 120 displays a plurality of second sub-pages (a second sub-page 72 is described as an example here) of the detail analysis page via the screen 140 and displays distribution information 721 of a plurality of variable features associated with one of the skin parameters via the second sub-page 72 according to the current measurement information. In the example shown in FIG. 7, the first sub-page 71 displays the historical record 711 of the skin parameter "firmness." Moreover, because the skin parameter "firmness" is calculated based on multiple variable features, the second sub-pages may respectively display the distribution information of the variable features associated with the skin parameter "firmness." For example, the second sub-page 72 displays the distribution information 721 of the variable feature "pores" associated with the skin parameter "firmness." The distribution information 721 includes a location of the variable feature "pores" on the face and a percentage corresponding to each facial block.

Figure 8:
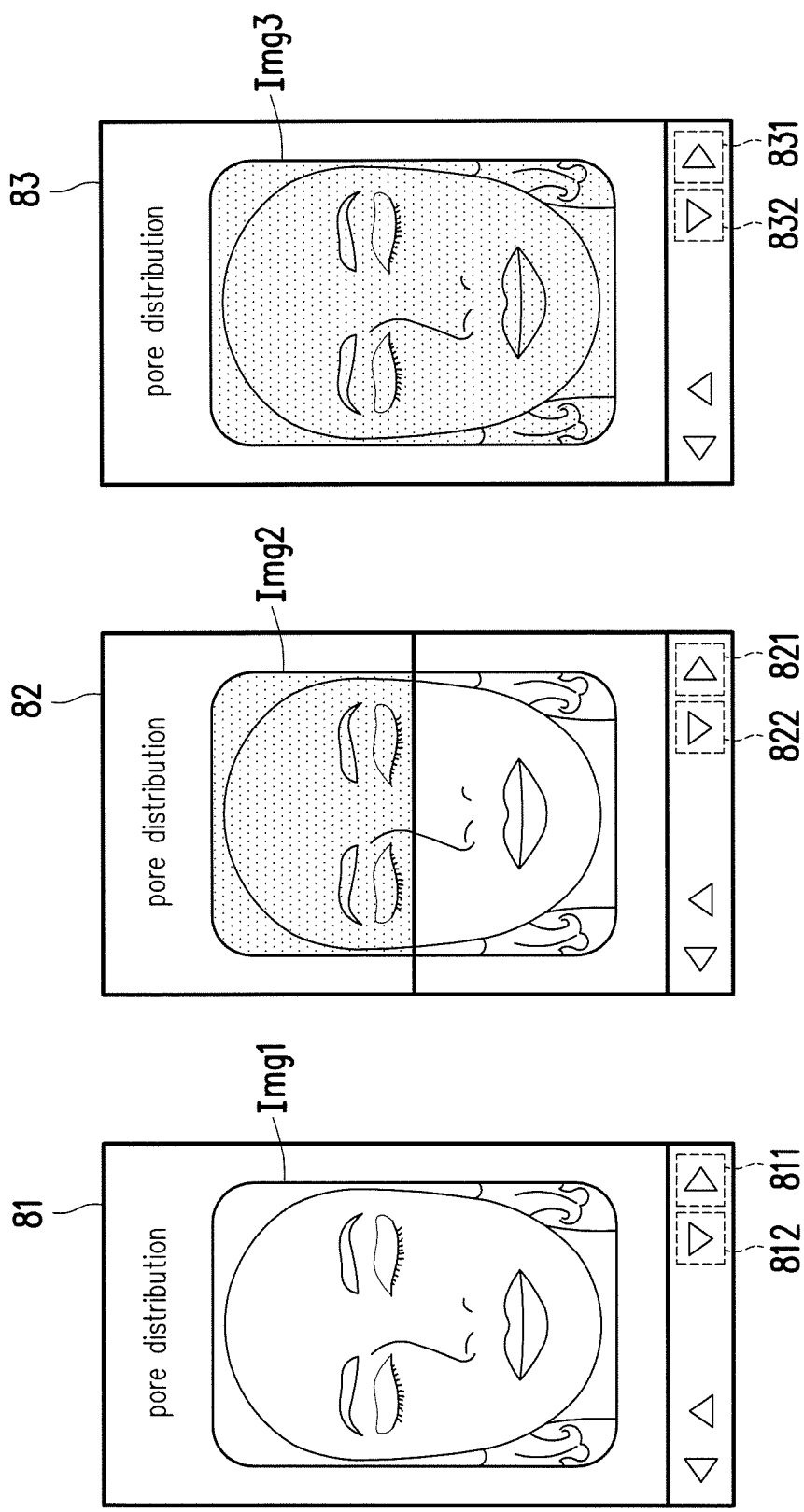
FIG. 8 is a schematic diagram showing the comparison page according to an embodiment of the disclosure.

Thereafter, referring to FIG. 3B and FIG. 8, FIG. 8 is a schematic diagram showing a comparison page according to an embodiment of the disclosure. In Step S308, in response to receipt of an operation performed on one of the second sub-pages of the detail analysis page, the processor 120 displays a plurality of comparison pages 81 to 83 via the screen 140 and sequentially displays an initial facial image Img3, a past/present comparison image Img2, and a current facial image Img1 via the comparison pages 81 to 83. Take FIG. 7 as an example, the operation performed on the second sub-page 72 of the detail analysis page is a touch operation that the user performs on the icon 722. In other words, after the user touches the icon 722 of the second sub-page 72, the processor 120 displays the comparison pages 81 to 83 via the screen 140. It should be noted that a portion a1 of the past/present comparison image Img2 is a portion of the initial facial image Img3 and another portion b1 of the past/present comparison image Img2 is a portion of the current facial image Img1.

Moreover, the user may perform a touch operation on an icon 812, an icon 822, and an icon 832 to drive the processor 120 to control the screen 140 to switch between the comparison pages 81 to 83. Thereby, the user is able to clearly see the difference between the current condition and the past state of the facial skin through the comparison pages 81 to 83.

Figure 9:
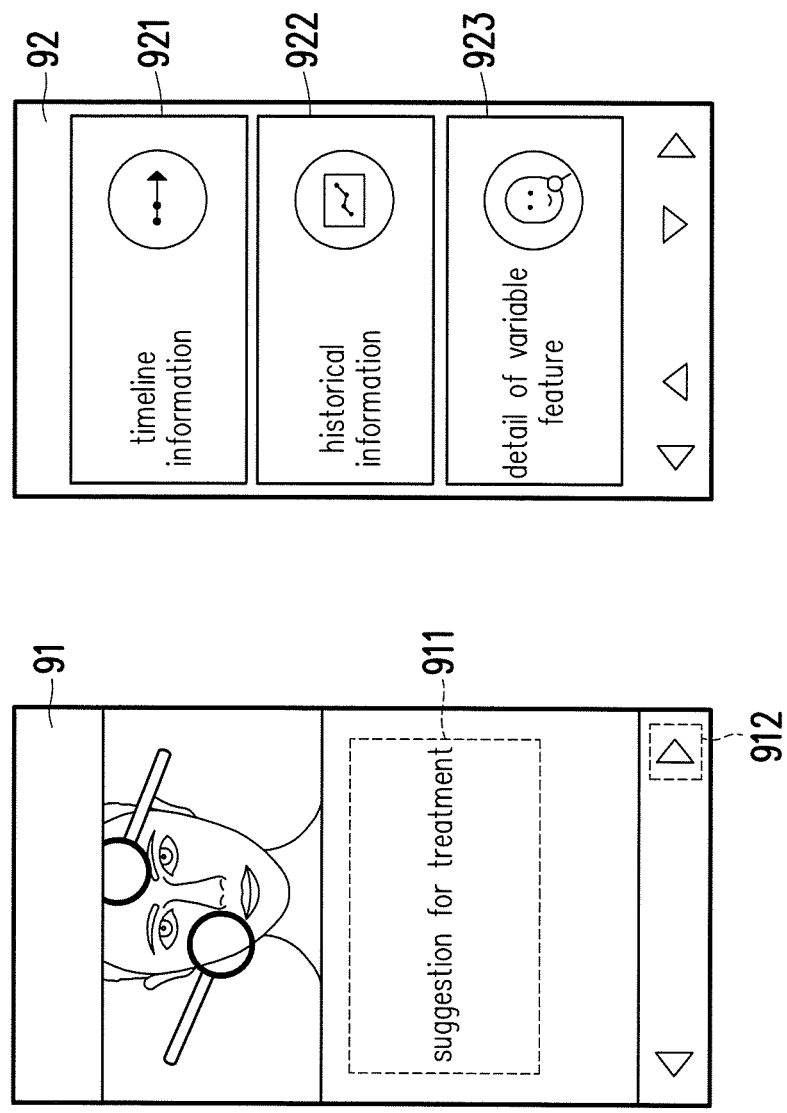
FIG. 9 is a schematic diagram showing the analysis and suggestion page according to an embodiment of the disclosure.

Thereafter, referring to FIG. 3B and FIG. 9, FIG. 9 is a schematic diagram showing an analysis and suggestion page according to an embodiment of the disclosure. In Step S309, in response to receipt of an operation performed on one of the comparison pages, the processor 120 displays a plurality of analysis and suggestion pages 91 to 92 via the screen 140 and displays a treatment suggestion 911 via one of the analysis and suggestion pages (i.e., the analysis and suggestion page 91) and displays a plurality of object options 921 to 923 via the other one of the analysis and suggestion pages (i.e., the analysis and suggestion page 92). Take FIG. 8 as an example, the operation performed on one of the comparison pages is a touch operation that the user performs on the icon 811, the icon 821, or the icon 831, for example. The treatment suggestion 911 may include a recommendation for skin care products or teaching of skin care methods. Moreover, by selecting the object options 921 to 923, the user may further check out different analysis information according to his/her needs. Take FIG. 9 as an example, when the user selects the object option 921, the processor 120 displays "timeline information" via the screen 140. When the user selects the object option 922, the processor 120 displays "historical information" via the screen 140. When the user selects the object option 923, the processor 120 displays "detail of variable feature" via the screen 140.

Figure 3C:
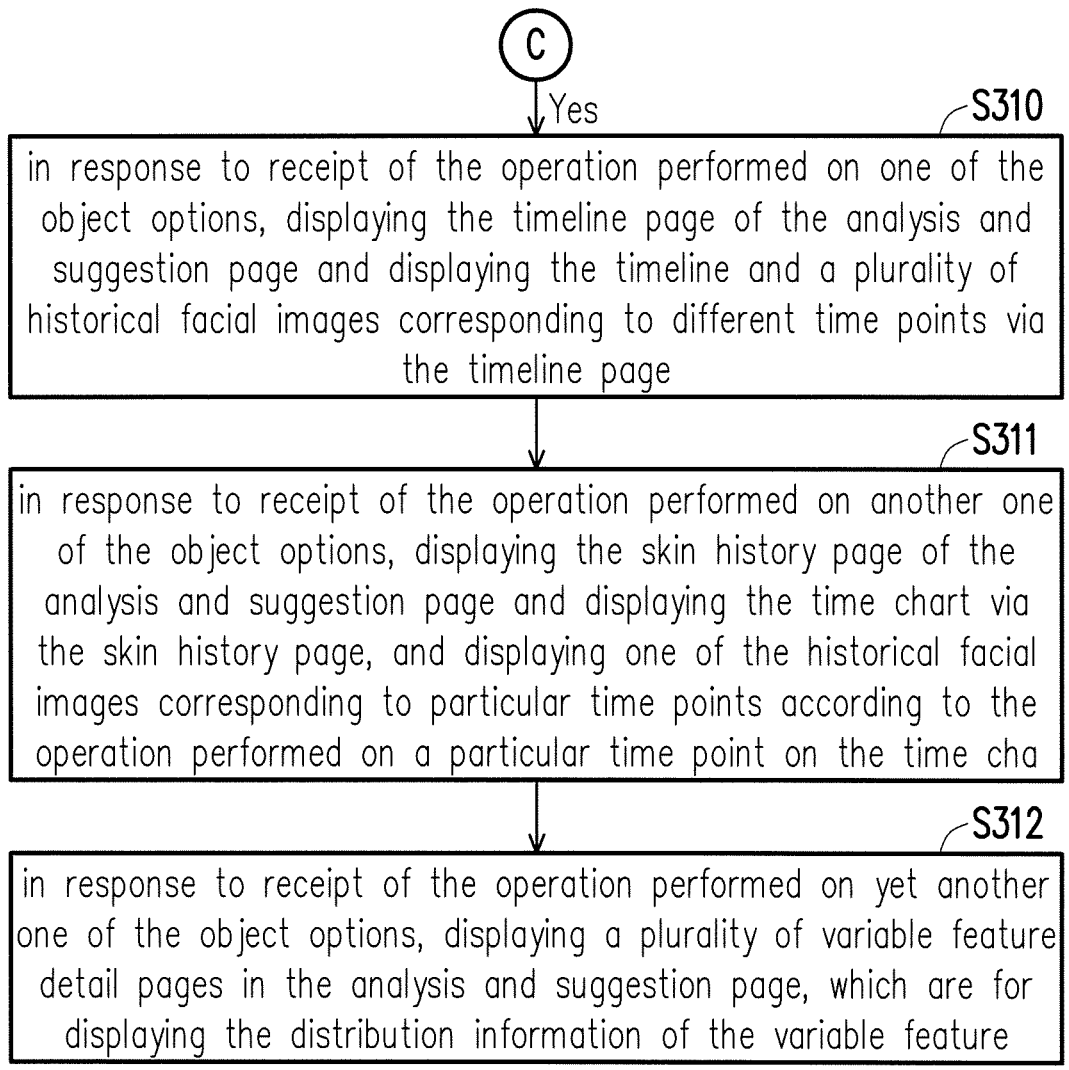
Figure 10:
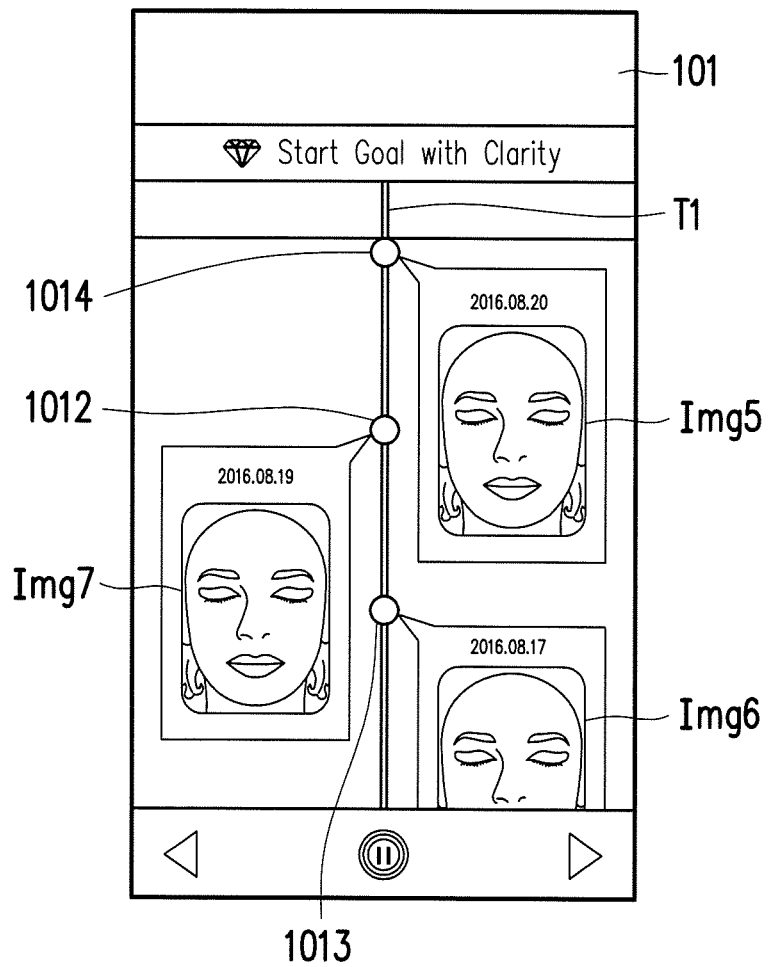
FIG. 10 is a schematic diagram showing the timeline page according to an embodiment of the disclosure.

More specifically, referring to FIG. 3C and FIG. 10, FIG. 10 is a schematic diagram showing the timeline page according to an embodiment of the disclosure. In Step S310, in response to receipt of an operation performed on one of the object options (i.e., the object option 921), the processor 120 displays a timeline page 101 of the analysis and suggestion page via the screen 140 and displays a timeline T1 and a plurality of historical facial images Img5 to Img7 corresponding to different time points 1011 to 1013 via the timeline page 101.

Figure 12:
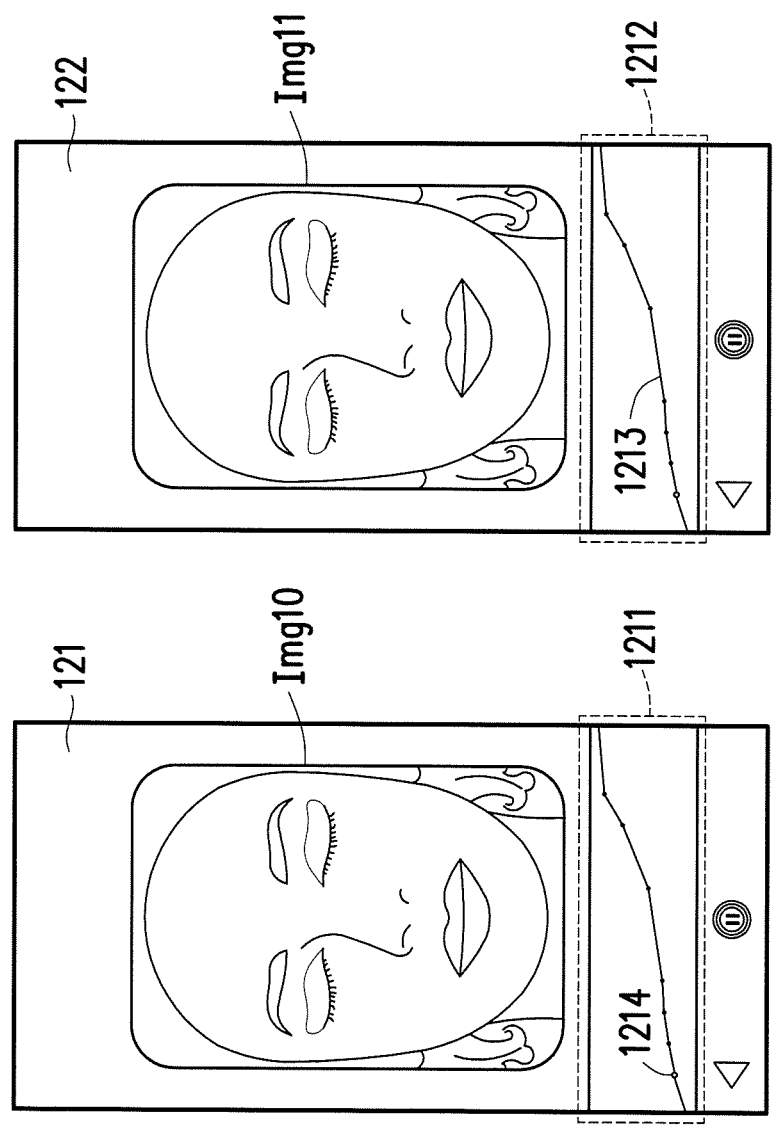
FIG. 12 is a schematic diagram showing the skin history page according to an embodiment of the disclosure.

Referring to FIG. 3C and FIG. 12, FIG. 12 is a schematic diagram showing a skin history page according to an embodiment of the disclosure. In Step S311, in response to receipt of an operation performed on another one of the object options (i.e., the object option 922), the processor 120 displays a skin history page 121 or a skin history page 122 of the analysis and suggestion page via the screen 140 and displays a time chart 1211 via the skin history pages 121 to 122, and displays one of the historical facial images Img10 to Img11 corresponding to particular time points 1214 and 1213 according to an operation performed on the particular time points 1214 and 1213 on the time chart 1211. Thereby, the user is able to drive the screen 140 to display the facial image captured at a particular time point by clicking on any particular time point on the time chart 1211.

Figure 11:
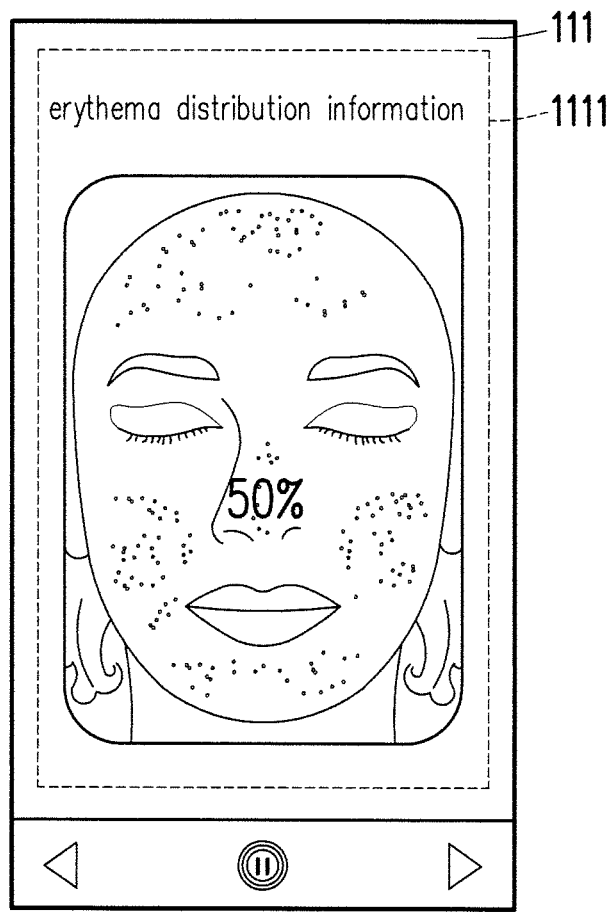
FIG. 11 is a schematic diagram showing the variable feature detail page according to an embodiment of the disclosure.

Referring to FIG. 3C and FIG. 11, FIG. 11 is a schematic diagram showing a variable feature detail page according to an embodiment of the disclosure. In Step S312, in response to receipt of an operation performed on yet another one of the object options (i.e., the object option 923), the processor 120 displays a plurality of variable feature detail pages (here, a variable feature detail page 111 is described as an example) in the analysis and suggestion page via the screen 140, which are for displaying the distribution information (here, the distribution information 1111 for example) of the variable feature. In the example of FIG. 11, the variable feature detail page 111 is for displaying the distribution information 1111 of the variable feature "erythema." Moreover, the user may perform a touch operation on an icon 1112 to drive the processor 120 to control the screen 140 to switch to other variable feature detail pages, so as to display the distribution information of other variable features.

Figure 3D:
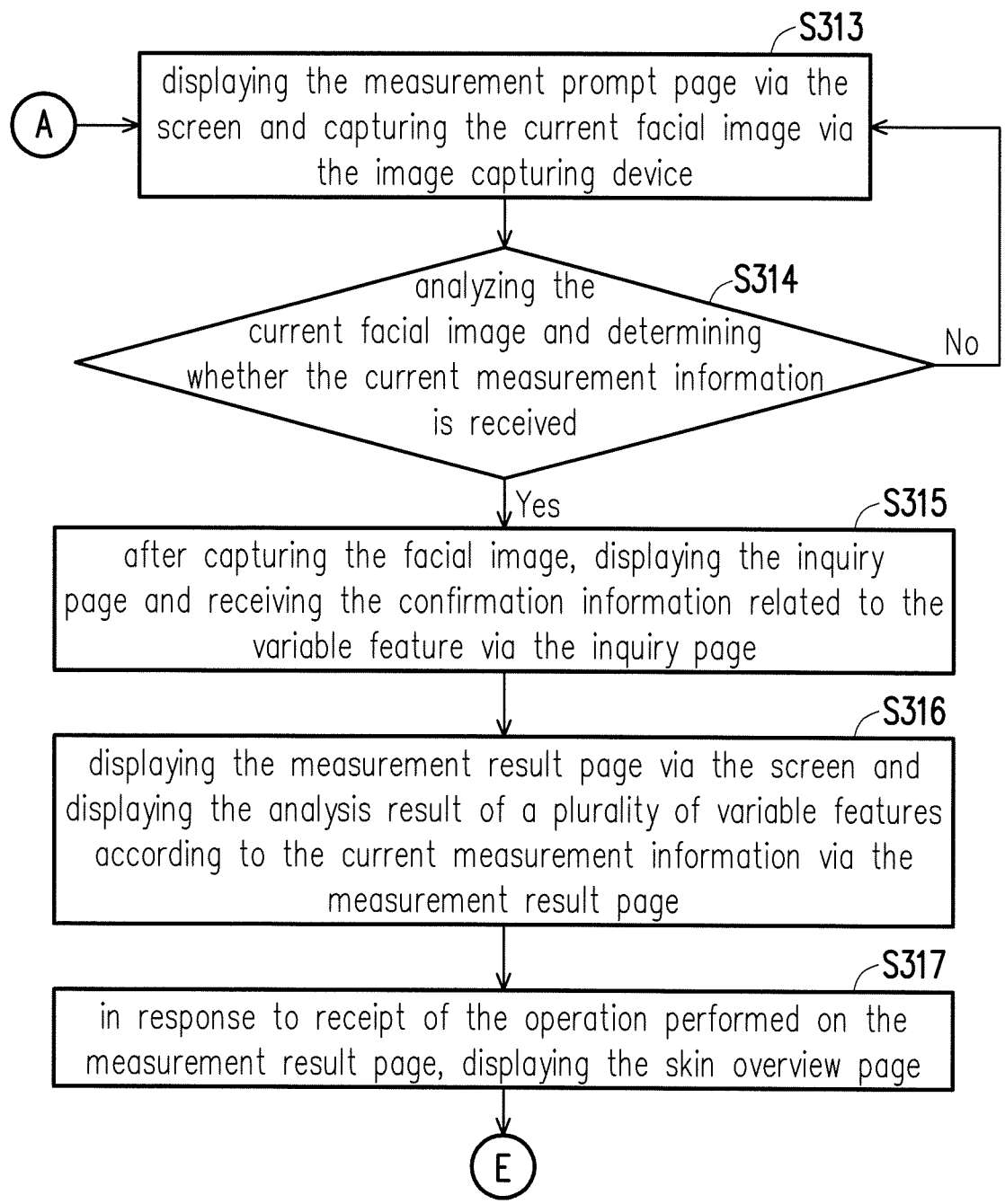
Figure 13:
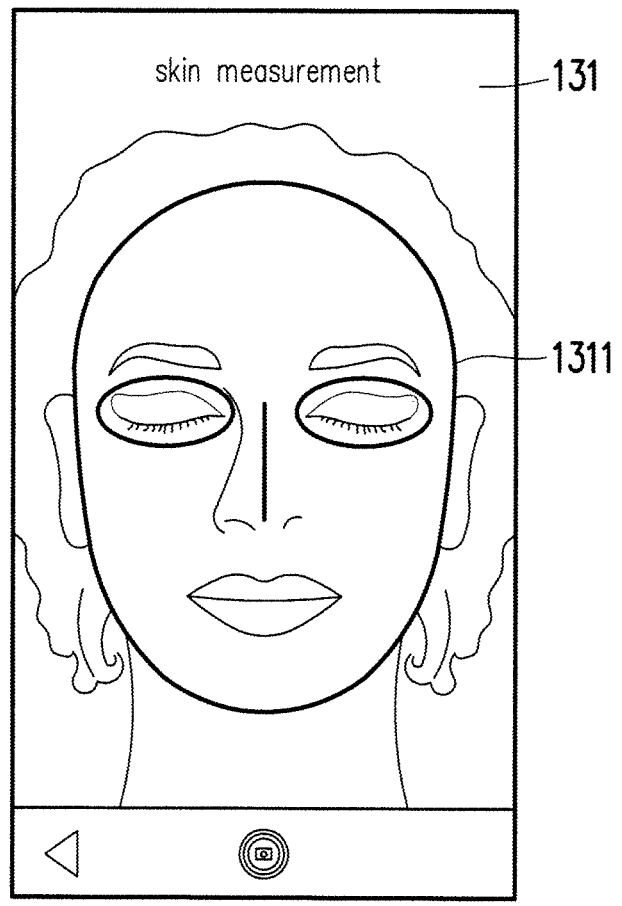
FIG. 13 is a schematic diagram showing the measurement prompt page according to an embodiment of the disclosure.

Referring to FIG. 3D and FIG. 13, FIG. 13 is a schematic diagram showing the measurement prompt page according to an embodiment of the disclosure. If the result of Step S301 of FIG. 3A is NO, it means that the processor 120 determines that the current measurement information is not received, and thus in Step S313, the processor 120 displays the measurement prompt page 131 via the screen 140 and captures the current facial image by the image capturing device 110. The measurement prompt page 131 displays a facial mark 1311 and simultaneously displays the image currently captured by the image capturing device 110. In other words, the facial mark 1311 of this embodiment is mainly used for marking locations of parts, such as the facial contour, eyes, nose bridge, and so on, in the facial mark 1311 presented on the screen 140, onto which the parts of the face of the user should be put. People who apply this embodiment may use other types of facial marks, such as a facial mark that only includes the facial contour or the eye locations. Thereby, the current user is able to align the user's face part with the facial mark 1311 for the processor 120 to more accurately obtain the facial information and subsequently determine the initial skin information.

Then, in Step S314, the processor 120 analyzes the current facial image and determines whether the current measurement information is received. It should be noted that the processor 120 may not be able to obtain the current measurement information due to poor image quality or erroneous image content. If the result of Step S314 is YES, in Step S315, after capturing the facial image, the processor 120 displays an inquiry page via the screen 140 and receives confirmation information related to the variable feature via the inquiry page. More specifically, the inquiry page is for further inquiring about the user's feeling with respect to a skin problem detected on the facial image, so as to confirm to which variable feature the detected skin problem belongs.

Figure 14:
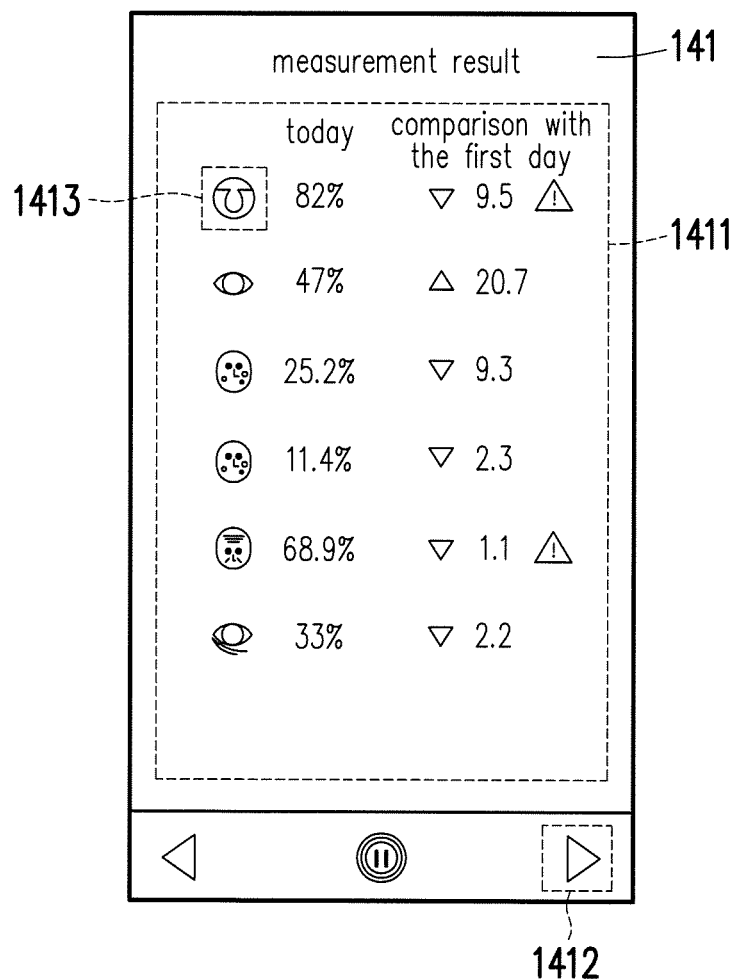
FIG. 14 is a schematic diagram showing the measurement result page according to an embodiment of the disclosure.

Thereafter, referring to FIG. 3D and FIG. 14, FIG. 14 is a schematic diagram showing the measurement result page according to an embodiment of the disclosure. In Step S316, the processor 120 displays a measurement result page 141 via the screen 140 and displays an analysis result 1411 of a plurality of variable features according to the current measurement information via the measurement result page 141. For example, the measurement result page 141 displays a present day analysis result of the variable feature "pores" 1413 and a degree of change with respect to the first day of the treatment. In Step S317, in response to receipt of an operation performed on the measurement result page 141, the processor 120 displays the skin overview page and returns to Step S304. The operation performed on the measurement result page 141 is a touch operation that the user performs on the icon 1412, for example.

To sum up, in an embodiment of the disclosure, when the user wants to obtain the skin inspection information, the electronic apparatus shows whether the current detection result achieves the skin goal via the result assessment page first. Thereby, the user is able to learn the progress of improvement of the skin condition immediately. Then, in response to receipt of the operation performed on the result assessment page, the electronic apparatus displays the skin overview page including the radar diagram of multiple skin parameters via the screen. Accordingly, the user may learn the overall condition of the facial skin intuitively and clearly. Further, in response to receipt of the first operation or the second operation performed on the skin overview page, the electronic apparatus displays the goal setting page or the detail analysis page of any one of the skin parameters via the screen. Therefore, through arrangement and design of each displayed page, the user is able to obtain accurate and objective skin inspection information by performing simple operations, and thereby to determine whether the skin care product used in the current treatment is effective.

It will be apparent to those skilled in the art that various modifications and variations can be made to the disclosed embodiments without departing from the scope or spirit of the disclosure. In view of the foregoing, it is intended that the disclosure covers modifications and variations of this disclosure provided that they fall within the scope of the following claims and their equivalents.

What is claimed is:

1. A skin inspection information providing method, for an electronic apparatus that comprises an image capturing device, an input device and a screen, the skin inspection information providing method comprising:

obtaining current measurement information comprising a plurality of skin parameters of a facial skin according to an image of the facial skin captured by the image capturing device and displaying a result assessment page of a detection result of the current measurement information via the screen, and showing whether the detection result achieves a skin goal via the result assessment page by comparing the skin goal set by a user with the current measurement information to obtain the detection result of the current measurement information, wherein the skin parameters are numeric calculated based on severity of a plurality of variable features of the facial skin obtained by analyzing different areas of the image;

in response to receipt of an operation performed on the result assessment page via the input device, displaying a skin overview page via the screen, wherein the skin overview page displays the skin parameters of the facial skin;

in response to receipt of a first operation performed on the skin overview page via the input device, displaying a goal setting page via the screen and receiving setting of the skin goal via the goal setting page; and in response to receipt of a second operation performed on the skin overview page via the input device, displaying a detail analysis page associated with one of the skin parameters via the screen, wherein the step of receiving the setting of the skin goal via the goal setting page comprises:

displaying a plurality of goal options respectively corresponding to the skin parameters via the goal setting page, wherein the goal options are icons displayed on the screen; and in response to receipt of an operation performed on one of the goal options via the input device, setting one of the skin parameters corresponding to the one of the goal options as the skin goal and setting a corresponding achievement value as the skin goal, wherein the step of displaying the result assessment page of the detection result of the current measurement information via the screen and showing whether the detection result achieves the skin goal via the result assessment page by comparing the skin goal set by the user with the current measurement information to obtain the detection result of the current measurement information comprises:

if the one of the skin parameters of the detection result achieves the corresponding achievement value of the skin goal, displaying an achievement notification via a first sub-page of the result assessment page; and if the one of the skin parameters of the detection result does not achieve the corresponding achievement value of the skin goal, displaying a treatment course report via a third sub-page of the result assessment page or displaying a comment via a fourth sub-page of the result assessment page, wherein after the step of displaying the detail analysis page associated with one of the skin parameters via the screen, the skin inspection information providing method further comprises:

in response to receipt of an operation performed on one of second sub-pages of the detail analysis page, displaying a plurality of comparison pages via the screen and sequentially displaying an initial facial image, a past/present comparison image, and a current facial image via the comparison pages, wherein a portion of the past/present comparison image is a portion of the initial facial image and another portion of the past/present comparison image is a portion of the current facial image.

2. The skin inspection information providing method according to claim 1, wherein if it is determined that the current measurement information of the facial skin is received, the step of displaying the result assessment page of the detection result of the current measurement information via the screen to show whether the detection result achieves the skin goal via the result assessment page comprises:

in response to receipt of an operation performed on the first sub-page, displaying the treatment course report of the facial skin via a second sub-page of the result assessment page wherein the step of if the detection result does not achieve the skin goal, displaying the treatment course report via the third sub-page of the result assessment page or displaying the comment via the fourth sub-page of the result assessment page comprises:

if the detection result does not achieve the skin goal, determining whether a treatment time expires;

if the treatment time expires, displaying the treatment course report of the facial skin via the third sub-page of the result assessment page; and if the treatment time does not expire, displaying the comment according to the detection result via the fourth sub-page of the result assessment page.

3. The skin inspection information providing method according to claim 1, further comprising:

if it is determined that the current measurement information of the facial skin is not received, displaying a measurement prompt page via the screen and capturing a current facial image by the image capturing device;

analyzing the current facial image and determining whether the current measurement information is obtained;

if it is determined that the current measurement information of the facial image is obtained, displaying a measurement result page via the screen and displaying an analysis result of a plurality of variable features according to the current measurement information via the measurement result page; and in response to receipt of an operation performed on the measurement result page, displaying the skin overview page.

4. The skin inspection information providing method according to claim 3, wherein before displaying the measurement result page, the skin inspection information providing method further comprises:

after capturing the facial image, displaying an inquiry page and receiving confirmation information related to the variable features via the inquiry page.

5. The skin inspection information providing method according to claim 1, wherein the step of displaying the detail analysis page associated with one of the skin parameters via the screen comprises:

displaying a historical record of one of the skin parameters via a first sub-page of the detail analysis page; and in response to receipt of an operation performed on the first sub-page of the detail analysis page, displaying a plurality of second sub-pages of the detail analysis page and displaying distribution information of a plurality of variable features associated with one of the skin parameters via the second sub-pages according to the current measurement information.

6. The skin inspection information providing method according to claim 5, wherein after the step of displaying the detail analysis page associated with one of the skin parameters via the screen, the skin inspection information providing method further comprises:

in response to receipt of an operation performed on one of the comparison pages, displaying a plurality of analysis and suggestion pages via the screen and displaying a treatment suggestion via one of the analysis and suggestion pages and displaying a plurality of object options via another one of the analysis and suggestion pages.

7. The skin inspection information providing method according to claim 6, wherein after the step of displaying the object options via the another one of the analysis and suggestion pages, the skin inspection information providing method further comprises:

in response to receipt of an operation performed on one of the object options, displaying a timeline page of the analysis and suggestion pages and displaying a timeline and a plurality of historical facial images corresponding to different time points via the timeline page;

in response to receipt of an operation performed on another one of the object options, displaying a skin history page of the analysis and suggestion pages and displaying a time chart via the skin history page, and according to an operation performed on a particular time point on the time chart, displaying one of the historical facial images corresponding to the particular time point; and in response to receipt of an operation performed on yet another one of the object options, displaying a plurality of variable feature detail pages in the analysis and suggestion pages for displaying the distribution information of the variable features.

8. The skin inspection information providing method according to claim 1, wherein the skin overview page displays a radar diagram drawn according to the skin parameters.

9. An electronic apparatus, comprising:
an image capturing device;
an input device;
a screen;
a storage device; and
a processor coupled to the image capturing device, the screen, and the storage device, wherein if the processor determines that current measurement information comprising a plurality of skin parameters of a facial skin is received, the processor displays a result assessment page of a detection result of the current measurement information via the screen to show whether the detection result achieves a skin goal via the result assessment page by comparing the skin goal set by a user with the current measurement information to obtain the detection result of the current measurement information, wherein the skin parameters are numeric calculated based on severity of a plurality of variable features of the facial skin obtained by analyzing different areas of the image, wherein in response to receipt of an operation performed on the result assessment page via the input device, the processor displays a skin overview page via the screen, wherein the skin overview page displays the skin parameters of the facial skin, wherein in response to receipt of a first operation performed on the skin overview page via the input device, the processor displays a goal setting page via the screen and receives setting of the skin goal via the goal setting page, and in response to receipt of a second operation performed on the skin overview page via the input device, the processor displays a detail analysis page associated with one of the skin parameters via the screen, wherein the processor displays a plurality of goal options respectively corresponding to the skin parameters via the goal setting page, wherein the goal options are icons displayed on the screen, and in response to receipt of an operation performed on one of the goal options, sets one of the skin parameters corresponding to the one of the goal options as the skin goal and a corresponding achievement value as the skin goal, wherein if the one of the skin parameters of the detection result achieves the corresponding achievement value of the skin goal, the processor displays an achievement notification via a first sub-page of the result assessment page, wherein if the one of the skin parameters of the detection result does not achieve the corresponding achievement value of the skin goal, the processor displays a treatment course report via a third sub-page of the result assessment page or displays a comment via a fourth sub-page of the result assessment page, wherein in response to receipt of an operation performed on one of second sub-pages of the detail analysis page, the processor displays a plurality of comparison pages via the screen and sequentially displays an initial facial image, a past/present comparison image, and a current facial image via the comparison pages, wherein a portion of the past/present comparison image is a portion of the initial facial image and another portion of the past/present comparison image is a portion of the current facial image.

10. The electronic apparatus according to claim 9, wherein in response to receipt of an operation performed on the first sub-page, the processor displays the treatment course report of the facial skin via a second sub-page of the result assessment page; and if the detection result does not achieve the skin goal, the processor determines whether a treatment time expires, wherein if the treatment time expires, the processor displays the treatment course report of the facial skin via the third sub-page of the result assessment page; and if the treatment time does not expire, the processor displays the comment according to the detection result via the fourth sub-page of the result assessment page.

11. The electronic apparatus according to claim 9, wherein if the processor determines that the current measurement information of the facial skin is not received, the processor displays a measurement prompt page via the screen and captures a current facial image by the image capturing device, and analyzes the current facial image and determines whether the current measurement information is obtained, wherein if the processor determines that the current measurement information of the facial image is obtained, the processor displays a measurement result page via the screen and displays an analysis result of a plurality of variable features according to the current measurement information via the measurement result page, and in response to receipt of an operation performed on the measurement result page, displays the skin overview page.

12. The electronic apparatus according to claim 11, wherein after capturing the facial image, the processor displays an inquiry page via the screen and receives confirmation information related to the variable features via the inquiry page.

13. The electronic apparatus according to claim 9, wherein the processor displays a historical record of one of the skin parameters via a first sub-page of the detail analysis page, wherein in response to receipt of an operation performed on the first sub-page of the detail analysis page, the processor displays a plurality of second sub-pages of the detail analysis page via the screen and displays distribution information of a plurality of variable features associated with one of the skin parameters via the second sub-pages according to the current measurement information.

14. The electronic apparatus according to claim 13, wherein in response to receipt of an operation performed on one of the comparison pages, the processor displays a plurality of analysis and suggestion pages via the screen and displays a treatment suggestion via one of the analysis and suggestion pages and displays a plurality of object options via another one of the analysis and suggestion pages.

15. The electronic apparatus according to claim 14, wherein in response to receipt of an operation performed on one of the object options, the processor displays a timeline page of the analysis and suggestion pages via the screen and displays a timeline and a plurality of historical facial images corresponding to different time points via the timeline page, wherein in response to receipt of an operation performed on another one of the object options, the processor displays a skin history page of the analysis and suggestion pages via the screen and displays a time chart via the skin history page, and according to an operation performed on a particular time point on the time chart, displays one of the historical facial images corresponding to the particular time point, wherein in response to receipt of an operation performed on yet another one of the object options, the processor displays a plurality of variable feature detail pages in the analysis and suggestion pages for displaying the distribution information of the variable features via the screen.

* * * * *